United States Patent [19]
Fischell

[11] Patent Number: 6,120,533
[45] Date of Patent: Sep. 19, 2000

[54] STENT DELIVERY SYSTEM FOR A RADIOISOTOPE STENT

[75] Inventor: Robert E. Fischell, Dayton, Md.

[73] Assignee: IsoStent, Inc., Belmont, Calif.

[21] Appl. No.: 09/193,672

[22] Filed: Nov. 13, 1998

[51] Int. Cl.⁷ .................................................. A61F 2/06
[52] U.S. Cl. .................................. 623/1.11; 606/108
[58] Field of Search .................... 606/108, 195, 606/198, 194; 623/1.11

[56] References Cited

U.S. PATENT DOCUMENTS

| | | |
|---|---|---|
| 3,811,426 | 5/1974 | Culvar et al. . |
| 5,059,166 | 10/1991 | Fischell et al. . |
| 5,199,939 | 4/1993 | Dake et al. . |
| 5,213,561 | 5/1993 | Weinstein et al. . |
| 5,302,168 | 4/1994 | Hess . |
| 5,571,086 | 11/1996 | Kaplan et al. ............................ 606/108 |
| 5,605,530 | 2/1997 | Fischell et al. .............................. 600/3 |
| 5,662,580 | 9/1997 | Bradshaw et al. . |
| 5,730,698 | 3/1998 | Fischell et al. ........................... 608/108 |
| 5,810,871 | 9/1998 | Tuckey et al. ............................ 606/108 |
| 5,840,008 | 11/1998 | Klein et al. ................................. 600/3 |
| 5,876,374 | 3/1999 | Alba et al. ................................ 606/194 |
| 5,879,282 | 3/1999 | Fischell et al. . |
| 5,951,569 | 9/1999 | Tuckey et al. ............................ 606/108 |

FOREIGN PATENT DOCUMENTS

| | | |
|---|---|---|
| 0775505 | 5/1997 | European Pat. Off. . |
| 0810004 | 12/1997 | European Pat. Off. . |
| 0832670 | 4/1998 | European Pat. Off. . |

*Primary Examiner*—Gene Mancene
*Assistant Examiner*—Eduardo C. Robert

[57] ABSTRACT

Disclosed is a stent delivery system consisting of a stent delivery catheter, a guide wire over which the stent delivery catheter is advanced and a balloon angioplasty catheter that is placed over the guide wire and within the stent delivery catheter. The stent delivery catheter is an elongated cylindrical tube with a radioisotope stent placed at a distal section of the tube. Just proximal and just distal to the stent there is a proximal radioactive marker band and a distal radioactive marker band each of which are fixedly attached to the delivery catheter. After the stent has been properly positioned at the site of a vascular blockage such as an arterial stenosis, a balloon angioplasty catheter can be advanced over the guide wire and inside the delivery catheter. The balloon at a distal section of the balloon angioplasty catheter is then inflated which expands the stent and both radioactive marker bands radially outward against the wall of the blood vessel. By the use of this device, the regions of the vessel wall that are just proximal and just distal to the edges of the stent are given a sufficient dose of radiation so that the cells in that region become incapable of producing growth factor. By this method, the edge effect that is frequently encountered with a radioisotope stent is avoided.

14 Claims, 5 Drawing Sheets

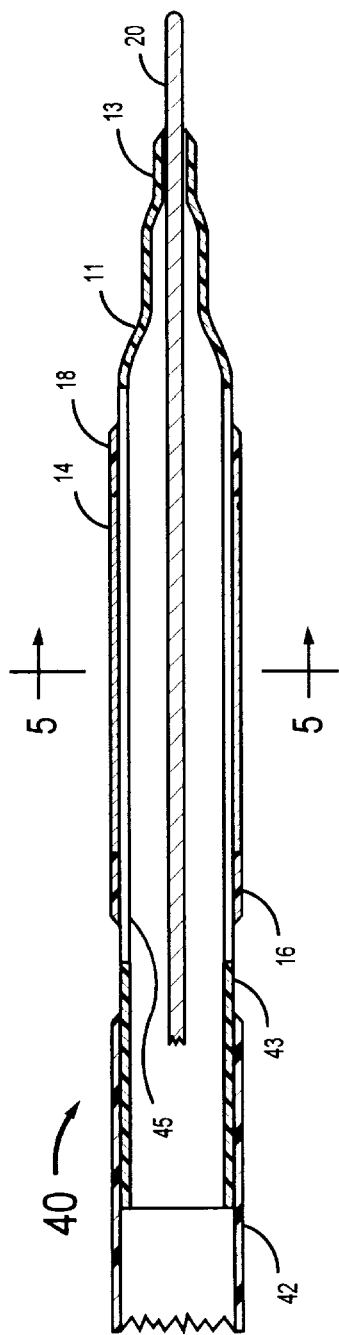
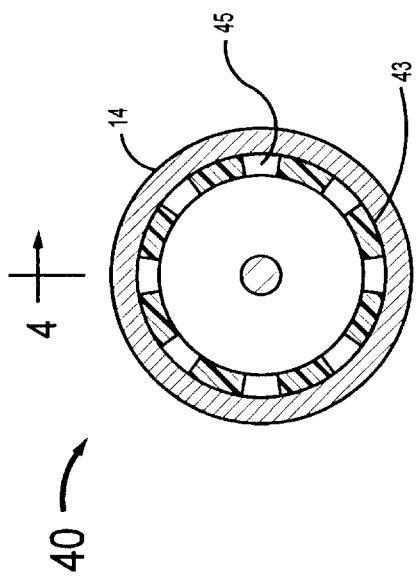
FIG. 4
FIG. 5

STENT DELIVERY SYSTEM FOR A RADIOISOTOPE STENT

FIELD OF USE

This invention is in the field of devices to treat vascular obstructions.

BACKGROUND OF THE INVENTION

In U.S. Pat. No. 5,059,166 by Fischell et al there is described a radioisotope stent for the treatment of arterial stenoses. In recent clinical trials, this radioisotope stent has been shown to decrease neointimal hyperplasia within the stent but in some patients an "edge effect" has been observed. The edge effect is characterized by a short length of stenosis that appears just proximal or just distal to the edge of the stent. When the edge effect is severe, the blood flow in that artery can be severely diminished.

SUMMARY OF THE INVENTION

The present invention is a stent delivery system for placing a radioactive stent into a vessel of a human body. The stent delivery system consists of a stent delivery catheter, a guide wire over which the stent delivery catheter is advanced and a balloon angioplasty catheter that is placed over the guide wire and within the stent delivery catheter. The stent delivery catheter is an elongated cylindrical tube with a radioisotope stent placed at a distal section of the tube. Just proximal and just distal to the stent there is a proximal radioactive marker band and a distal radioactive marker band each of which are fixedly attached to the delivery catheter. The stent delivery system, which includes the radioisotope stent, is designed to be advanced over a guide wire that had been previously placed through the human vasculature system in order to place the stent at the site of a vascular obstruction. After the stent has been properly positioned at the site of a vascular blockage such as an arterial stenosis, a balloon angioplasty catheter can be advanced over the guide wire and inside the delivery catheter. The balloon that is situated at a distal section of the balloon angioplasty catheter is then advanced until it is centered within the stent. The balloon is then inflated which expands the stent radially outward into the wall of the blood vessel. The balloon remains expanded for several minutes which maintains the proximal radioactive marker band and the distal radioactive marker band against the arterial wall at a position that is just proximal to and just distal to the edges of the stent. By this means, the regions of the vessel wall that are just proximal and just distal to the edges of the stent experience a sufficient dose of radiation so that the cells in that region become incapable of producing growth factor. By this means, the edge effect that is frequently encountered with a radioisotope stent is avoided.

After the edge regions of the vessel wall have been sufficiently irradiated, the balloon is deflated and the delivery catheter, balloon angioplasty catheter and the guide wire are all removed from the patient's vascular system.

Thus it is an object of this invention to use a single stent delivery system to both place a radioisotope stent at the site of a vascular obstruction and to irradiate the regions of the vessel wall that are just proximal and just distal to the edges of the stent.

Another object of this invention is to teach a method for eliminating the edge effect that occurs in some human subjects in whom radioisotope stents are implanted.

Still another object of this invention is to have a stent delivery system that eliminates the edge effect and also has the capability for allowing the perfusion of distal tissue during the time when the procedure is taking place.

Still another object of this invention is to have a single size for the stent delivery system, which stent delivery system can be used with inflatable balloons having a variety of different diameters so as to deploy the stent.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 4 is a longitudinal cross section of an alternative embodiment of the present invention that is a stent delivery catheter having a slotted distal section. The longitudinal cross section of FIG. 4 is taken at section 4—4 of FIG. 5.

FIG. 5 is a transverse cross section of the stent delivery catheter as shown at section 5—5 of FIG. 4.

DETAILED DESCRIPTION OF THE DRAWINGS

Figure 1:
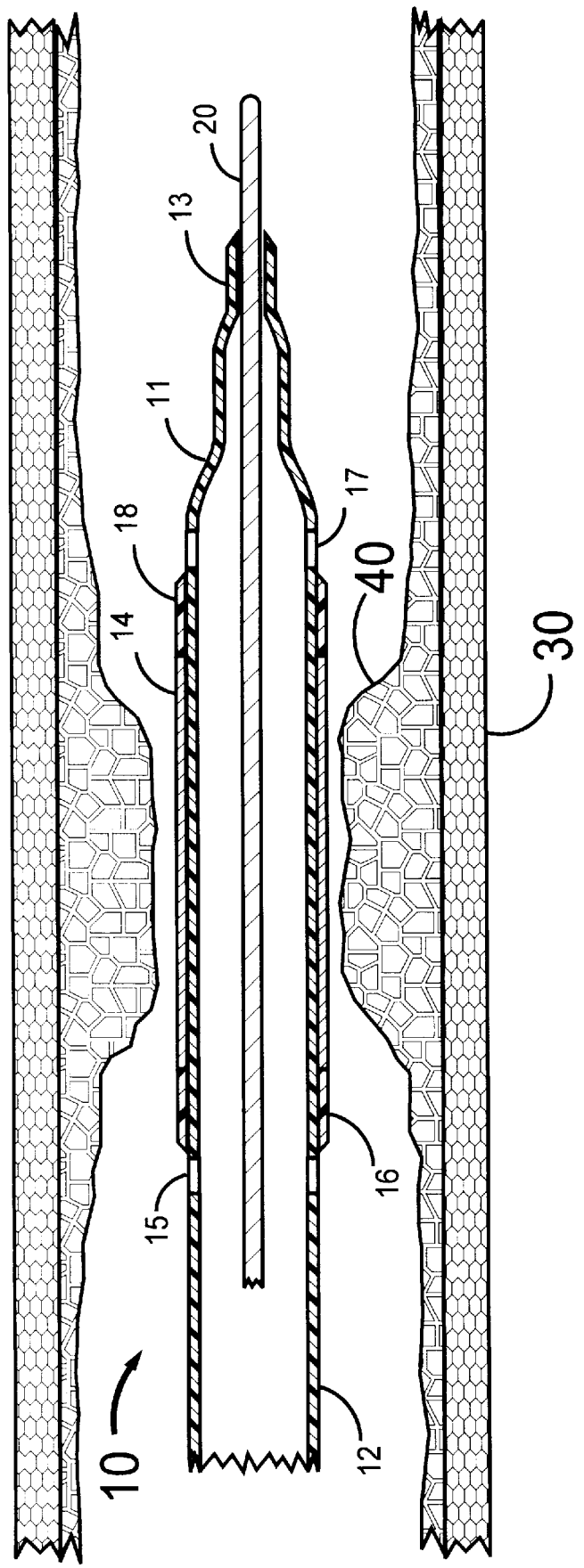
FIG. 1 is longitudinal cross section of a stent delivery catheter having a distal section at which section is located a radioisotope stent that is situated between a proximal radioactive marker band and a distal radioactive marker band.
Figure 2:
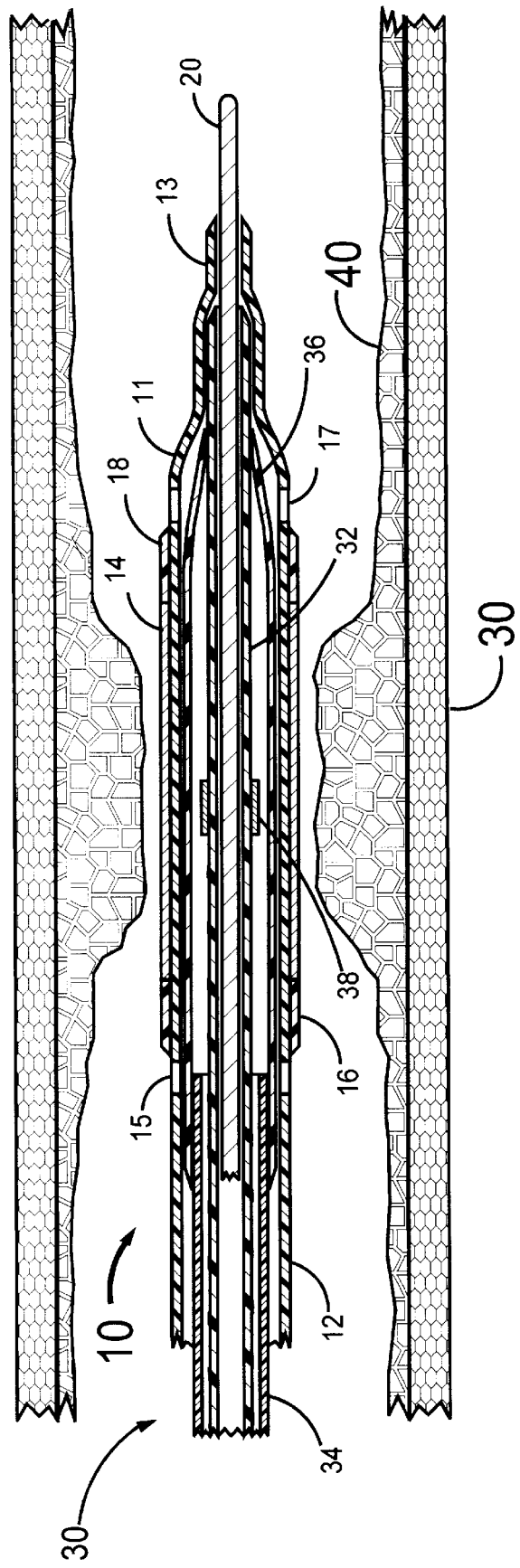
FIG. 2 is a longitudinal cross section of the stent delivery catheter of FIG. 1 into which a balloon angioplasty catheter has been placed.
Figure 3:
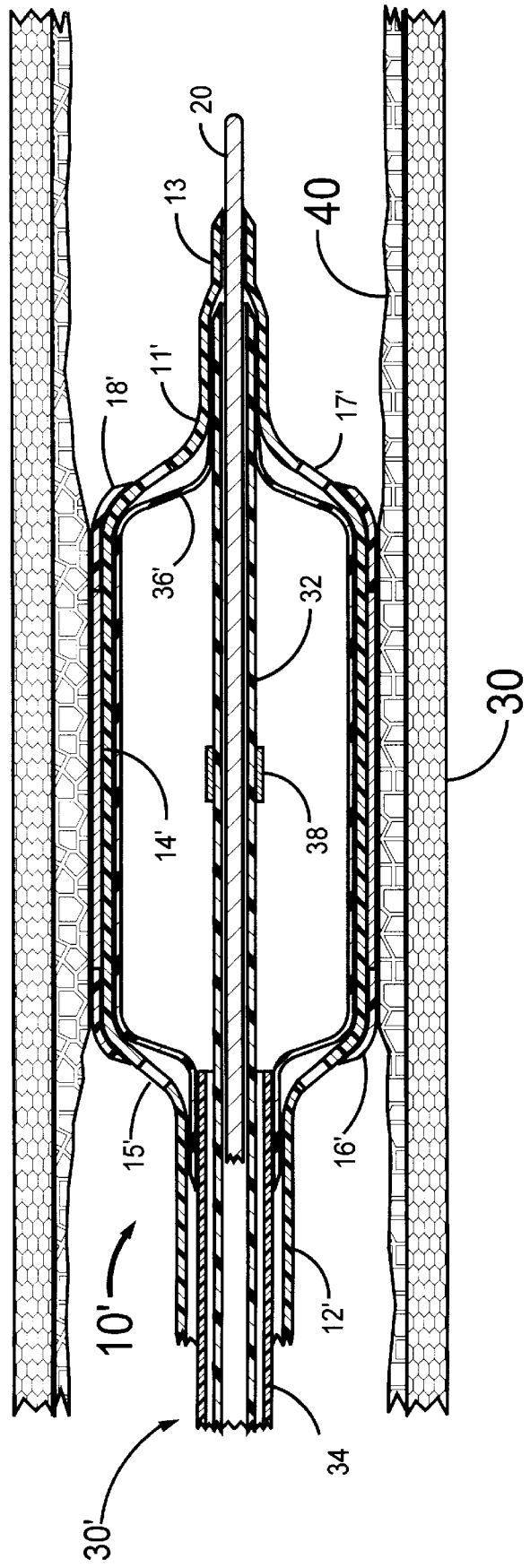
FIG. 3 is a longitudinal cross section of the stent delivery catheter plus balloon angioplasty catheter of FIG. 2 shown with the balloon at the distal section of the balloon angioplasty catheter being inflated.

FIG. 1 is a longitudinal cross section of a distal section of a stent delivery catheter 10 having a delivery catheter 12 that has a tapered nose 11 with a cylindrical distal section 13. In FIGS. 1, 2 and 3, the stent delivery catheter 10 is shown in an artery having an arterial wall 30 and deposited plaque 40. The elongated cylindrical delivery catheter 12 also has a set of proximal holes 15 and a set of distal holes 17. Mounted onto a distal section of the delivery catheter 12 is a radioisotope stent 14, a proximal radioactive marker band 16 and a distal radioactive marker band 18. The marker bands 16 and 18 would be fixedly attached to the delivery catheter 12 by thermal bonding or by means of an adhesive. Co-axially situated within the delivery catheter 12 is a guide wire 20.

FIG. 2 is a longitudinal cross section of the distal section of a stent delivery system that consists of the stent delivery catheter 10, the guide wire 20 and a balloon angioplasty catheter 30 that has been placed over the guide wire 20 and co-axially within the stent delivery catheter 10. The balloon angioplasty catheter 30 has an inner shaft 32, an outer shaft 34, an inflatable balloon 36 and a radiopaque marker band 38.

FIG. 3 is longitudinal cross section of the distal section of the stent delivery catheter 10', the guide wire 20 and the balloon angioplasty catheter 30' showing the radioisotope stent 14' expanded radially outward against the arterial wall as a result of the inflation of the inflatable balloon 36'. The inflated balloon 36' also causes the proximal radioactive marker band 16' and the distal radioactive marker band 18' to be pushed against the arterial wall at the regions just beyond the edges of the deployed radioisotope stent 14'. In this position, the marker bands 16' and 18' can irradiate the arterial wall tissue just proximal and just distal to the edges of the radioisotope stent 14' thereby disabling the cells in that region from producing growth factors that can cause the "edge effect" in some patients. Also seen in FIG. 3 is the inner shaft 32, outer shaft 34 and radiopaque marker band 38 of the balloon angioplasty catheter 30'. FIG. 3 also shows a multiplicity of proximal holes 15' and a multiplicity of distal holes 17'. The holes 15' and 17' allow the flow of blood through the distal section of the stent delivery catheter 10' when the balloon angioplasty catheter 30' is of the perfusion type. Although the invention described herein could perform satisfactorily without such capability to perfuse tissue distal to the distal section of the stent delivery catheter 10', a capability for perfusion would allow the balloon 36' to remain inflated for an extended period of time without causing discomfort to the patient. If perfusion capability is not provided, the balloon 36' may have to be deflated for some period of time and then re-inflated to obtain additional dosing of the arterial wall in the regions just proximal and just distal to the edges of the stent.

FIG. 4 is a longitudinal cross section of an alternative embodiment stent delivery catheter 40. The stent delivery catheter 40 differs from the stent delivery catheter 10 in two respects. Firstly, the delivery catheter 12 is replaced by a two-piece delivery catheter consisting of a proximal cylindrical tube 42 that is attached to a distal section tube 43. The proximal section tube 42 would be reasonably stiff longitudinally so as to provide good pushability for the stent delivery catheter 40. The proximal section tube 42 could be made from a relatively stiff plastic or a plastic impregnated with metal wire in order to provide good pushability. The distal section tube 43 would be highly elastic so as to allow for the deployment of the stent 14 without requiring excessively high balloon inflation pressure. Secondly, the stent delivery catheter 40 has a distal section tube 43 that has longitudinally extending slots 45. These slots also allow for easier deployment of the stent 14.

FIG. 5 is a highly enlarged transverse cross section of the stent delivery catheter 40 showing the non-deployed stent 14 placed around a slotted distal section tube 43. It should be understood that the slotted tube design can be used with a stent delivery catheter that is formed from either one or two elongated tubes. Furthermore, stent delivery catheters can be formed from two separate tubes without having longitudinally extending slots 45 formed in the distal section tube 43.

Figure 6:
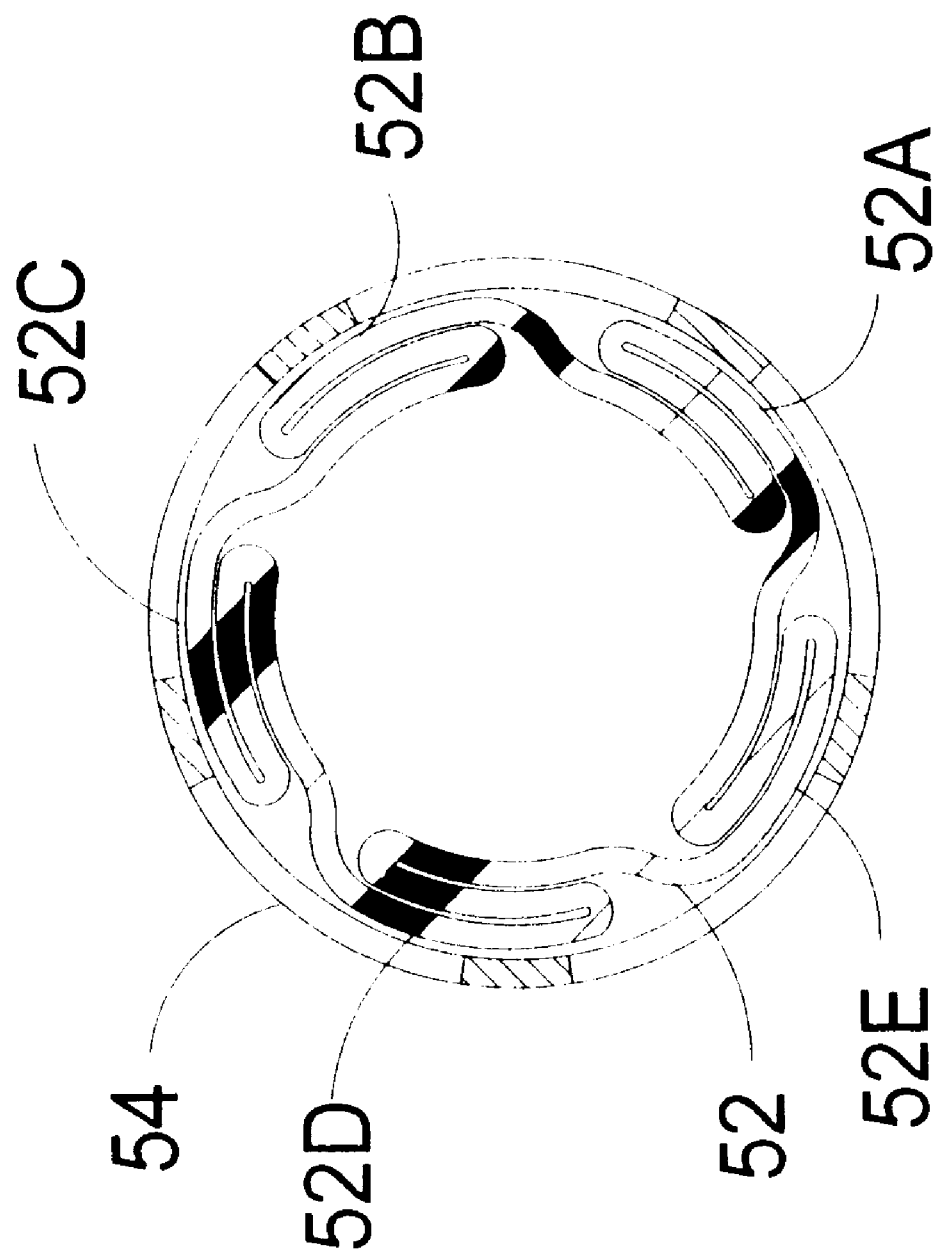
FIG. 6 is a transverse cross section of a distal section of another alternative embodiment of the present invention in which the distal section of the stent delivery catheter has a multiplicity of folds placed within an expandable stent.

FIG. 6 is a transverse cross section of a distal section of another alternative embodiment of the present invention in which the distal section of the stent delivery catheter has a multiplicity of folds placed within an expandable stent. Specifically, FIG. 6 shows a distal section 52 of a stent delivery catheter that has a stent 54 that surrounds a multiplicity of folds 52A, 52B, 52C, 52D and 52E, which folds are similar in form and function to folds placed in a non-deployed balloon of a balloon angioplasty catheter. Thus, when the balloon of a balloon angioplasty catheter is inflated within the structure shown in FIG. 6, the distal section 52 has each of its folds straightened and moved radially outward to form a cylindrical structure of uniform wall thickness. This would cause the stent 54 (and the radioactive marker bands that are not shown) to be deployed against the arterial wall.

The proximal radioactive marker band 16 and the distal radio active marker band 18 would be molded from a highly elastic elastomer such as silicone rubber into which a powder from a high density metal is placed. Such a metal could be tungsten, tantalum or any other highly radiopaque metal. Furthermore, a radioisotope such as the beta particle emitter phosphorous-32 or yttrium-90 could be impregnated into the marker bands 16 and 18. Thus, the marker bands 16 and 18 would be both radiopaque and radioactive. The radiopacity would indicate the position of the stent 14 on the delivery catheter 12. Radioactivity is used to irradiate the arterial wall in the region just proximal and just distal to the edges of the stent. Although a beta particle emitting radioisotope is desirable, there are several gamma or x-ray emitters having a comparatively short range in human tissue that could also be employed. In any case, a level of radioactivity of between 1 and 100 milliCuries would be suitable for each of the marker bands 16 and 18. Since the radioisotope stent, especially prior to deployment, is clearly visible by fluoroscopy, the marker bands 16 and 18 need not necessarily be radiopaque; i.e., they need not necessarily include a high density metal.

The procedure for using this invention would be as follows:

1. a guide wire 20 is inserted into the patient's vascular system until its distal end lies distal to the blockage (typically an arterial stenosis) in the blood vessel;

2. the stent delivery catheter 10 is advanced over the guide wire 20 until the stent 14 is longitudinally centered in the blockage;

3. the balloon angioplasty catheter 30 is advanced over the guide wire and within the stent delivery catheter 10 until the radiopaque marker band 38 is centered between the proximal radioactive marker band 16 and the distal radioactive marker band 18;

4. the balloon 36 is inflated to form the inflated balloon 36' which pushes the deployed stent 14' and the expanded marker bands 16' and 18' against the arterial wall;

5. the balloon 36' remains inflated for a sufficient length of time to provide a radiation dose of between 300 cGy and 3,000 cGy to the arterial wall just distal and just proximal to the edges of the stent 14'; and 6. the balloon 36' is then deflated, and the stent delivery catheter 10, the balloon angioplasty catheter 30 and the guide wire 20 are all removed from the patient's vascular system while the deployed stent 14' remains within the dilated blockage.

One advantage of this invention is that a single diameter of the stent delivery catheter 10 can be used with balloon angioplasty catheters 30 having a range of diameters for the inflatable balloon. For example, if the diameter of the stent delivery catheter 12 (or 40) was 1.0 mm, it could be used with balloon angioplasty catheters having diameters for the inflated balloon 36' that might be as small as 2.0 mm and as large as 4.0 mm. A stent delivery catheter 12 (or 40) having a diameter of 2.0 mm could be used with diameters for the inflated balloon 36' that would be between 4.0 and 8.0 mm.

Various other modifications, adaptations, and alternative designs are of course possible in light of the above teachings. Therefore, it should be understood at this time that within the scope of the appended claims the invention could be practiced otherwise than as specifically described herein.

What is claimed is:

1. A system for maintaining the patency of a blood vessel of a human body, the system comprising:

a flexible guide wire;

a stent delivery catheter in the form of an elongated cylindrical tube having a distal section and having a longitudinally directed central lumen for slideable insertion therethrough of the flexible guide wire, the stent delivery catheter also including a deployable radioisotope stent mounted onto the distal section of the cylindrical tube and a proximal radioactive marker band mounted just proximal to the stent and a distal radioactive marker band mounted just distal to the stent; and a balloon angioplasty catheter having a distal section and having an inflatable balloon placed at the distal section of the balloon angioplasty catheter, the balloon angioplasty catheter being adapted to be placed co-axially over the guide wire and within the stent delivery catheter, the inflatable balloon being adapted to expand the radioisotope stent and both marker bands against the wall of a blood vessel when the inflatable balloon is inflated.

2. The stent delivery system of claim 1 wherein the proximal radioactive marker band and the distal radioactive marker band are both radioactive and radiopaque so as to be clearly seen in fluoroscopy.

3. The stent delivery system of claim 1 wherein both marker bands include a beta particle emitting radioisotope.

4. The stent delivery system of claim 3 wherein the beta particle emitting isotope is phosphorous-32.

5. The stent delivery system of claim 3 wherein the beta particle emitting isotope is yttrium-90.

6. The stent delivery system of claim 1 wherein both marker bands include a gamma ray emitting radioisotope.

7. The stent delivery system of claim 1 wherein both marker bands include an x-ray emitting radioisotope.

8. The stent delivery system of claim 1 wherein each of the radioactive marker bands has a radioactive activity level that lies between 1 and 100 milliCuries.

9. The stent delivery system of claim 1 wherein the elongated cylindrical tube of the delivery catheter is formed with a distal section that includes longitudinally extending slots.

10. The stent delivery system of claim 1 wherein the delivery catheter of the stent delivery system is formed with a first proximally located tube formed from a first plastic material that is fixedly attached to a second, distally located tube that is formed from a second plastic material.

11. The stent delivery system of claim 1 wherein the distal section of the delivery catheter includes a multiplicity of folds that are placed within the radioisotope stent prior to the deployment of the radioisotope stent.

12. The stent delivery system of claim 1 wherein the delivery catheter is adapted to provide blood perfusion by means of a first multiplicity of holes located proximal to the proximal radioactive marker band and a second multiplicity of holes located distal to the distal radioactive marker band.

13. A method for dilating an arterial stenosis in the vascular system of a human body and also eliminating the edge effect experienced when a radioisotope stent is placed at the site of the dilated stenosis, the method comprising the following steps:

(a) placing a guide wire through the vascular system of the human body until the distal end of the guide wire lies distal to the arterial stenosis;

(b) advancing a stent delivery catheter over the guide wire until a radioisotope stent located at a distal section of the stent delivery catheter is longitudinally centered at the site of the arterial stenosis, the stent delivery catheter also including a proximal radioactive marker band located just proximal to the radioisotope stent and a distal radioactive marker band located just distal to the radioisotope stent;

(c) advancing a balloon angioplasty catheter over the guide wire and within the stent delivery catheter until an inflatable balloon located at a distal section of the balloon angioplasty catheter is longitudinally centered within the radioisotope stent of the stent delivery catheter;

(d) inflating the inflatable balloon until the radioisotope stent, the proximal radioactive marker band and the distal radioactive marker band are all expanded radially outward so as to be in close contact with the arterial wall at the site of the arterial stenosis;

(e) maintaining the balloon in its inflated state until the regions of the arterial wall just proximal and just distal to the edges of the radioisotope stent experience a radiation dose of between 300 cGy and 3,000 cGy;

(f) deflating the balloon; and (g) removing the stent delivery catheter, the balloon angioplasty catheter and the guide wire from the vascular system of the human body.

14. The method of claim 13 including the additional step of inflating and deflating the balloon of the balloon angioplasty catheter a total of at least two times before the stent delivery system is removed from the vascular system of the human body.

* * * * *